United States Patent
Yamamoto (10) Patent No.: US 9,402,768 B2
(45) Date of Patent: Aug. 2, 2016

(54) OPHTHALMIC LASER TREATMENT APPARATUS

(75) Inventor: Mitsuo Yamamoto, Gamagori (JP)

(73) Assignee: NIDEK CO., LTD., Gamagori-shi (JP)

( * ) Notice: Subject to any disclaimer, the term of this patent is extended or adjusted under 35 U.S.C. 154(b) by 716 days.

(21) Appl. No.: 13/334,754

(22) Filed: Dec. 22, 2011

(65) Prior Publication Data

US 2012/0165799 A1    Jun. 28, 2012

(30) Foreign Application Priority Data

Dec. 27, 2010    (JP) .................................. 2010-291373

(51) Int. Cl.
*A61B 18/20*    (2006.01)
*A61F 9/008*    (2006.01)

(52) U.S. Cl.
CPC ... *A61F 9/00821* (2013.01); *A61F 2009/00851* (2013.01); *A61F 2009/00863* (2013.01)

(58) Field of Classification Search
CPC ........ A61B 3/102; A61B 3/0025; A61B 3/12; A61B 3/14
USPC ..................... 606/2–19; 607/88–94
See application file for complete search history.

(56) References Cited

U.S. PATENT DOCUMENTS

| | | | |
|---|---|---|---|
| 5,493,109 A | 2/1996 | Wei et al. | |
| 6,004,314 A | 12/1999 | Wei et al. | |
| 7,794,083 B2 | 9/2010 | Tsukada et al. | |
| 2006/0119858 A1* | 6/2006 | Knighton et al. | 356/479 |
| 2007/0129709 A1* | 6/2007 | Andersen et al. | 606/4 |
| 2007/0252951 A1* | 11/2007 | Hammer et al. | 351/221 |
| 2008/0015553 A1* | 1/2008 | Zacharias | 606/4 |
| 2008/0151187 A1* | 6/2008 | Tsukada et al. | 351/206 |
| 2008/0167642 A1* | 7/2008 | Palanker et al. | 606/4 |
| 2009/0093798 A1 | 4/2009 | Charles | |
| 2009/0137988 A1 | 5/2009 | Kurtz | |
| 2009/0149840 A1 | 6/2009 | Kurtz | |
| 2010/0145319 A1 | 6/2010 | Zimare et al. | |
| 2010/0324542 A1 | 12/2010 | Kurtz | |
| 2014/0257258 A1 | 9/2014 | Kurtz | |

FOREIGN PATENT DOCUMENTS

| | | |
|---|---|---|
| DE | 10 2007 005 699 A1 | 8/2008 |
| EP | 0 697 611 A2 | 2/1996 |
| JP | 2006-095318 A | 4/2006 |
| JP | A-2008-029467 | 2/2008 |

(Continued)

OTHER PUBLICATIONS

Extended European Search Report issued in European Patent Application No. 11195249.5 dated May 15, 2012.

(Continued)

*Primary Examiner* — Aaron Roane
(74) *Attorney, Agent, or Firm* — Oliff PLC (57) ABSTRACT

An ophthalmic laser treatment apparatus includes an irradiation position obtaining unit arranged to obtain analysis result data based on a tomographic image of a patient's eye captured by an optical coherence tomography device before a treatment laser beam is irradiated, and obtain information of an irradiation position of the treatment laser beam with respect to the eye set by use of the obtained analysis result data, and a laser control unit arranged to irradiate the laser beam to the eye based on the irradiation position information obtained by the irradiation position obtaining unit.

19 Claims, 4 Drawing Sheets

(56) References Cited

FOREIGN PATENT DOCUMENTS

| JP | 2008-154704 A | 7/2008 |
| JP | B2-4126054 | 7/2008 |
| JP | A-2010-148635 | 7/2010 |
| JP | 2010-538699 A | 12/2010 |
| WO | 2009-059251 A2 | 5/2009 |
| WO | WO 2011/151064 A1 | 12/2011 |

OTHER PUBLICATIONS

Jul. 31, 2015 Office Action issued in European Patent Application No. 11195249.5.

* cited by examiner

OPHTHALMIC LASER TREATMENT APPARATUS

CROSS-REFERENCE TO RELATED APPLICATIONS

This application is based upon and claims the benefit of priority from the prior Japanese Patent Application No. 2010-291373, filed Dec. 27, 2010, the entire contents of which are incorporated herein by reference.

BACKGROUND

1. Technical Field

The present invention relates to an ophthalmic laser treatment apparatus to be used for irradiating a laser beam to a patient's eye.

2. Related Art

There is known a treatment laser device arranged to irradiate a treatment laser beam onto tissues (e.g., a fundus) of a patient's eye to treat the eye (see Patent Document 1). When using such a device, an operator observes a fundus front image through a slit lamp and a fundus camera and irradiates a laser beam to an area of the eye to be treated.

When a front observation optical system is used, only surface information of the patient's eye could be obtained. For instance, it is difficult to check photoreceptor cells of the eye in a front observation image. For treating retinopathia diabetica, laser irradiation is performed regardless of whether the photoreceptor cells are normal or not.

RELATED ART DOCUMENTS

Patent Documents

Patent Document 1: JP 2010-148635A

SUMMARY

The present invention has an object to provide an ophthalmic laser treatment apparatus capable of obtaining useful information for laser treatment of a patient's eye.

To achieve the above object, one aspect of the invention provides an ophthalmic laser treatment apparatus comprising: an irradiation optical system including a treatment light source and a deflector for deflecting a laser beam for treatment emitted from the light source with respect to a patient's eye, the irradiation optical system being arranged to irradiate the laser beam to an area of the eye to be treated; a setting unit arranged to obtain two-dimensional analysis result data of a fundus of the patient's eye based on a three-dimensional tomographic image captured by an optical coherence tomography device before the laser beam is irradiated, and arranged to set information of an irradiation position of the laser beam in a surface direction of the fundus based on the obtained analysis result data; and a controller adapted to control operation of the light source and the deflector to irradiate the laser beam to the eye based on the irradiation position information set by the setting unit.

According to the invention, it is possible to obtain useful information for laser treatment of a patient's eye.

DETAILED DESCRIPTION

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
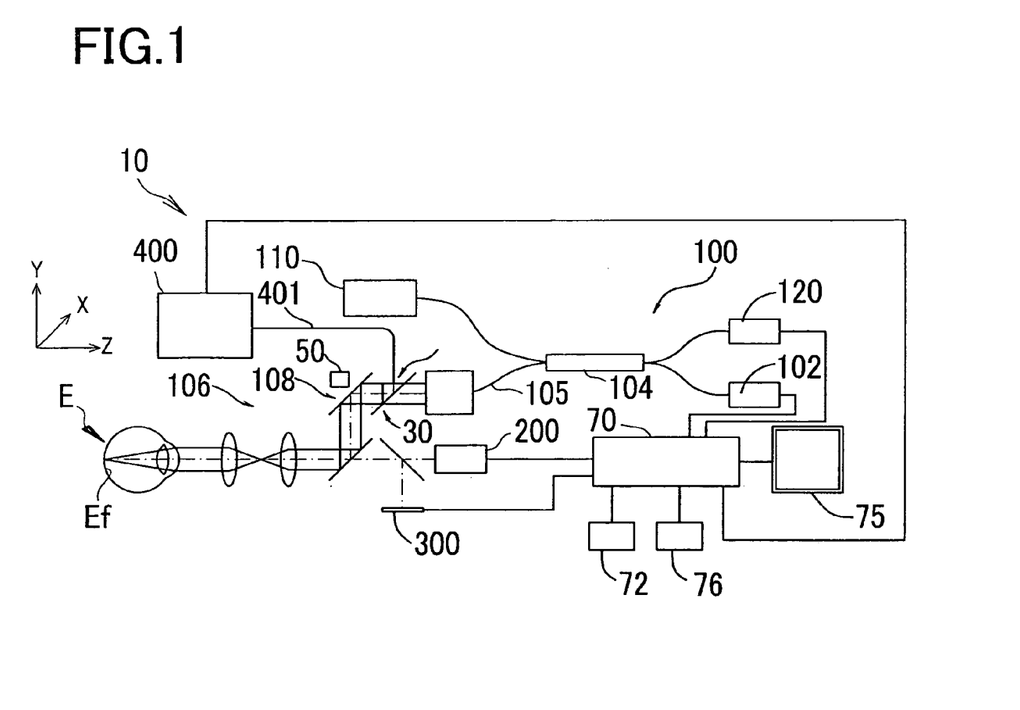
FIG. 1 is a schematic configuration diagram to explain an ophthalmic photographing device in an embodiment.

A preferred embodiment according to the present invention will be explained below referring to the accompanying drawings. FIG. 1 is a schematic configuration diagram to explain an ophthalmic photographing apparatus of the present embodiment, which is an example of an ophthalmic laser treatment apparatus of the invention. In this embodiment, an axial direction of an examinee's eye (an eye E) is referred to as a Z direction, a horizontal direction is referred to as an X direction, and a vertical direction is referred to as a Y direction. A surface direction of a fundus may also be considered as a X-Y direction.

The ophthalmic photographing apparatus is schematically configured as below. In the present embodiment, this apparatus is an optical coherence tomography device (an OCT device) 10 to image a tomographic image of a fundus Ef of the eye E. The OCT device 10 includes an optical coherence optical system (OCT optical system) 100, a front observation optical system 200, a fixation target projecting optical system 300, a photocoagulation laser device 400, and a calculation and control unit (CPU) 70.

The OCT optical system 100 is arranged to irradiate measurement light to a fundus Ef. In the OCT optical system 100, a light receiving element (a detector 120) detects an interference state between the measurement light reflected from the fundus Ef and reference light. To change an imaging position on the fundus Ef, the OCT optical system 100 includes an irradiation position changing unit (e.g., an optical scanner 108 and a fixation target projecting unit 300) for changing an irradiation position of the measurement light on the fundus Ef. The control unit 70 controls operations of the irradiation position changing unit based on the set imaging position information, and obtains a tomographic image based on a received signal from the detector 120. Further, the photocoagulation laser device 400 emits a treatment laser beam (a photocoagulation laser beam).

<OCT Optical System>

The OCT optical system 100 is configured as a so-called ophthalmic optical coherence tomography (OCT). In this embodiment, the OCT optical system 100 images a tomographic image of a patient's eye before the treatment laser beam is irradiated. The OCT optical system 100 splits the light emitted from a measurement light source 102 into measurement light (sample light) and reference light by a coupler (a light splitter) 104. The OCT optical system 100 delivers the measurement light to the fundus Ef of the eye E through a measurement optical system 106 and also delivers the reference light to a reference optical system 110. Thereafter, interference light formed as a result of synthesis of the measurement light reflected by the fundus Ef and the reference light is received by the detector (a light receiving element) 120.

The detector 120 detects the interference light depending on the interference state between the measurement light and the reference light. In the case of Fourier-domain OCT, a spectral intensity of the interference light is detected by the detector 120 and subjected to Fourier transform so that a depth profile (A-scan signal) in a predetermined range is obtained. Other examples of the OCT are Spectral-domain OCT (SD-OCT), Swept-source OCT (SS-OCT), and Time-domain OCT (TD-OCT).

In the case of SD-OCT, a low-coherent light source (a broadband light source) is used as the light source 102, and a spectral optical system (a spectrometer) configured to disperse the interference light into different frequency components (wavelength components) is provided in the detector 120. The spectrometer includes, for example, a diffraction grating and a line sensor.

In the case of SS-OCT, a wavelength scanning light source (a wavelength variable light source) configured to change an emission wavelength very fast is used as the light source 102, and a light receiving element alone, for example, is used as the detector 120. The light source 102 includes, for example, a light source, a fiber ring resonator, and a wavelength selectable filter. Examples of the wavelength selectable filter are a filter in which a diffracting grating and a polygonal mirror are combined, and a filter in which Fabry-Perot etalon is used.

The light emitted from the light source 102 is split into the measurement light beam and the reference light beam by the coupler 104. The measurement light beam passes through an optical fiber 105 and then is emitted into atmosphere. The light is converged on the fundus Ef via the optical scanner 108 and other optical components of the measurement optical system 106. The light reflected by the fundus Ef travels a similar optical path and then returns to the optical fiber 105.

The optical scanner 108 scans the measurement light on the fundus Ef in the X-Y direction (a traverse direction). The optical scanner 108 is disposed at a position substantially conjugate with a pupil. The optical scanner 108 consists of for example two galvano mirrors, and their reflection angles are arbitrarily adjusted by a drive mechanism 50.

Accordingly, the reflection direction (a traveling direction) of the light beam emitted from the light source 102 is changed to scan the fundus Ef in any arbitral direction. As a result, an imaging position on the fundus Ef is changed. The optical scanner 108 has only to be configured to deflect light. Examples of the optical scanner 108 are reflection mirrors (galvano mirror, polygon mirror, resonant scanner), an acousto-optic device (AOM) which changes a light traveling (deflecting) direction, and others.

The reference optical system 110 generates the reference light to be synthesized with the measurement light reflected from the fundus Ef. The reference optical system 110 may be a Michelson optical system or a Mach-Zehnder optical system. The reference optical system 110 is for example constituted of a reflective optical system (e.g., a reference mirror). The light output from the coupler 104 is reflected by the reflective optical system to return to the coupler 104 so that the light is guided to the detector 120. Another example of the reference optical system 110 is a transmission optical system (for example, an optical fiber), wherein the light output from the coupler 104 is not returned thereto but is transmitted through the transmission optical system to be guided to the detector 120.

The reference optical system 110 is configured to move the optical members present in a reference optical path to change a difference in optical path length between the measurement light and the reference light. For example, the reference mirror is moved in the direction of an optical axis. A device for changing the difference in optical path length may be provided in a measurement optical path of the measurement optical system 106.

<Front Observation Optical System>

The front observation optical system 200 is provided to obtain a front image of the fundus Ef. This optical system 200 includes for example an optical scanner for scanning the measurement light (e.g., infrared light) emitted from a light source two-dimensionally on the fundus Ef and a second light receiving element for receiving the reflection light from the fundus Ef through a confocal opening placed at a position substantially conjugate with the fundus Ef. Thus, the optical system 200 is configured as a so-called ophthalmic scanning laser optometry (SLO).

As an alternative, the observation optical system 200 may be configured as a fundus camera. The OCT optical system 100 can concurrently serve as an observation optical system 200, wherein the front image is captured based on the tomographic image data two-dimensionally obtained (for example, an integrated image of three-dimensional tomographic images in the depth direction, an integrated value of spectral data at each position in X and Y directions).

<Fixation Target Projecting Unit>

The fixation target projecting unit 300 includes an optical system for guiding a sight line of the eye E. This projecting unit 300 has fixation targets to be presented to the eye E whereby to guide the eye E to any of different directions.

For instance, the fixation target projecting unit 300 has a visible light source which emits visible light and is arranged to change the target presenting position two-dimensionally, thereby changing the sight line direction so that a site to be imaged (an imaging site) is changed. For example, when a fixation target is presented in the same direction as the imaging optical axis, a center part of the fundus Ef is set as the imaging site. Further, when the fixation is presented above the imaging optical axis, an upper part of the fundus Ef is set as the imaging site. That is, the imaging site is changed according to the position of the target with respect to the imaging optical axis.

For example, the fixation target projecting unit 300 is configured to adjust the fixation position by using LED lighting positions arranged in a matrix shape or adjust the fixation position by scanning the light from the light source using the optical scanner for lighting control of the light source. The projecting unit 300 may be an internal fixation lamp or an external fixation lamp.

<Photocoagulation Laser Device>

The photocoagulation laser device 400 has a light source and is arranged to emit a treatment laser beam (e.g., a wavelength of 532 nm). The light emitted from the light source of the photocoagulation laser device 400 is introduced in an optical fiber 401 and emitted from an emission end 401a. The laser beam emitted from the emission end 401a is reflected by a dichroic mirror 30, and then converged on the fundus Ef via the optical scanner 108 and other optical components of the measurement optical system 106. The optical scanner 108 serves as a light deflecting device to deflect the laser beam emitted from the light source toward the eye E. In this case, the measurement optical system 106 is used as an irradiation optical system for irradiating the laser beam to an area of an eye to be treated (a treatment area).

Accordingly, the laser beam emitted from the photocoagulation laser device 400 is changed in its reflection (traveling) direction by the optical scanner 108 and made to scan on the fundus Ef in two dimensions. Thus, an irradiation position of the laser beam on the fundus Ef is changed.

As an alternative, the photocoagulation laser device 400 may include an aiming light source that emits aiming light, in addition to the treatment light source.

<Control Unit>

The control unit 70 controls the entire apparatus such as components of each configuration 100 to 400. The control unit 70 also serves as an image processor for processing obtained images, an image analyzer for analyzing the obtained images, and others. The control unit 70 is implemented by a general CPU (Central Processing Unit) and others.

Figure 2A:
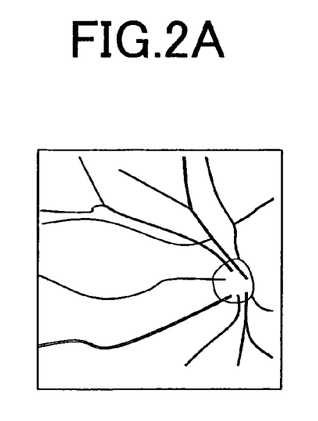
FIG. 2A shows an example of a front image obtained through a front observation optical system.
Figure 2B:
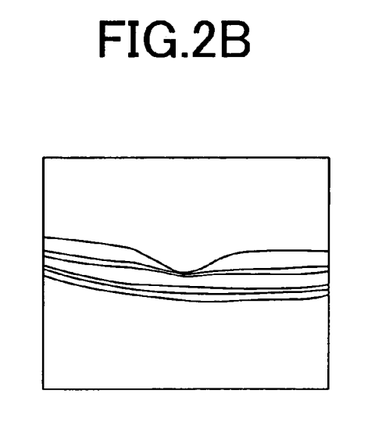
FIG. 2B shows an example of a tomographic image obtained through an OCT optical system.

FIG. 2A is an example of a front image obtained by the front observation optical system 200 and FIG. 2B is an example of a tomographic image obtained by the OCT optical system 100. For instance, the control unit 70 obtains a tomographic image (an OCT image) by image processing based on a received signal output from the detector 120 of the OCT optical system 100 and also obtains a front image based on a received signal output from the light receiving element of the front observation optical system 200. The control unit 70 controls the fixation target projecting unit 300 to change a fixation position.

A memory (a storage part) 72, a monitor (a display part) 75, an operation part 76 are respectively electrically connected to the control unit 70. The control unit 70 controls a display screen of the monitor 75. An obtained fundus image is output as a still image or a moving image on the monitor 75 and additionally stored in the memory 72. The memory 72 records e.g. imaged tomographic images, front images, various information related to imaging such as information on an imaging position of each tomographic image, etc. The control unit 70 controls each component of the OCT optical system 100, the front observation optical system 200, and the fixation target projecting unit 300, based on an operation signal output from the mouse 76. Further, a touch panel is used as the monitor 75. For the details of the configuration of the above OCT device 10, refer to JP 2008-29467A for example.

The present embodiment exemplifies an examinee's eye with retinopathia diabetica. The procedures for treating the retinopathia diabetica by a laser beam will be explained below.

<Obtaining of Tomographic Image>

The control unit 70 controls the OCT optical system 100 to obtain a three-dimensional tomographic image corresponding to each set region and also controls the observation optical system 200 to obtain a front image. The three-dimensional tomographic image includes an image data in which A-scan signals arranged two-dimensionally in the X-Y directions, a three-dimensional graphic image, and others.

To obtain the three-dimensional tomographic image, the control unit 70 controls operations of the optical scanner 108 to scan the measurement light two-dimensionally in the X-Y directions in a scanning range corresponding to the imaging region, thereby obtaining the three-dimensional tomographic image. Available scanning patterns are for example a raster scan pattern, a multiple-line scan pattern, or the like.

<Determination of Photoreceptor Cells>

The control unit 70 includes an image analyzer. After obtaining the tomographic image, the control unit 70 detects information of the layers of a fundus in the obtained tomographic image by image processing. The OCT device 100 analyzes a detection result of the layers based on a predetermined image determination condition (criterion). For an example of analysis, the control unit 70 detects the layer information at each position in the X-Y directions and analyzes the state of photoreceptor cells at each position based on the detected layer information. Then, the analysis result is stored in a memory of the OCT device 100 or an external memory (e.g., a memory of a personal computer, a memory of a server) together with the three-dimensional tomographic image.

For detecting the layers, for instance, a luminance level of the tomographic image is detected and a layer corresponding to a predetermined retinal layer (e.g., a junction between inner and outer segments of the photoreceptor cells, hereinafter referred to as "IS/OS") is extracted.

When the tomographic image is to be determined, this determination may be carried out for example by determining whether each layer is present or absent, determining the thickness of each layer, determining the shape of each layer, determining the size of a predetermine portion (e.g., papilla, macula), etc. The control unit 70 for instance detects a luminance distribution of each A-scan signal and determines whether the IS/OS is present according to whether a rise in luminance corresponding to the IS/OS is detected.

Figure 3A:
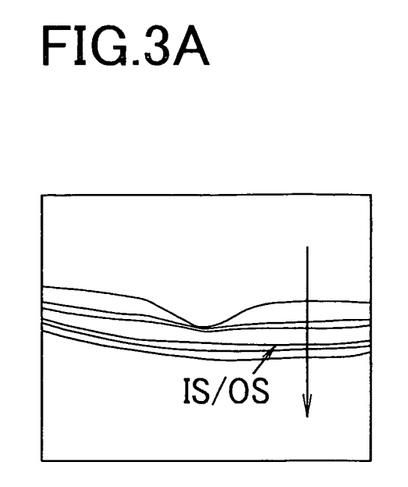
FIG. 3A shows a tomographic image in which IS/OS is present.
Figure 3B:
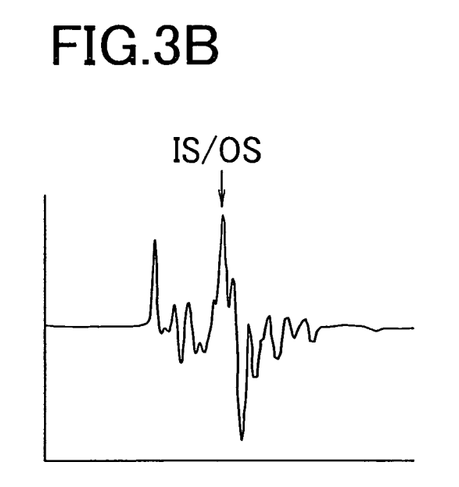
FIG. 3B is a graph showing a luminance distribution in the case where the IS/OS is present.
Figure 3C:
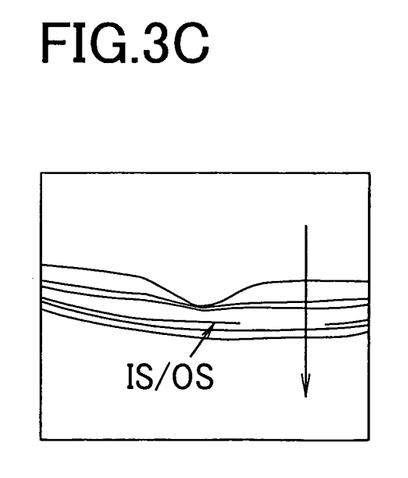
FIG. 3C shows a tomographic image in which the IS/OS is absent.
Figure 3D:
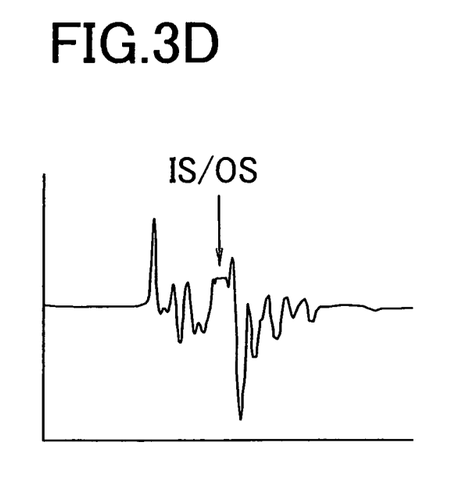
FIG. 3D is a graph showing a luminance distribution in the case where the IS/OS is absent.

FIG. 3A shows a tomographic image in which the IS/OS is present and FIG. 3B is a graph showing a luminance distribution in a state where the IS/OS is present. FIG. 3C shows a tomographic image in which the IS/OS is absent and FIG. 3D is a graph showing a luminance distribution in a state where the IS/OS layer is absent. In other words, when the IS/OS remains, a peak corresponding to the IS/OS appears. When the IS/OS has disappeared, on the other hand, no peak corresponding to the IS/OS is detected but a peak corresponding to RPE (retinal pigment epithelium) appears. The presence/absence of the IS/OS can be specified by use of the order of the layers anatomically known, the distance from a retinal surface, a sharp rise of luminance corresponding to the IS/OS, and others.

The control unit 70 analyzes the fundus tomographic image and performs determination processing related to sites with normal/abnormal visual function to obtain, as analysis result data, positional information on the normal/abnormal sites of visual function on the fundus of the patient's eye.

The control unit 70 regards a site at which the IS/OS is determined to be present as an area where photoreceptor cells are likely to normally function.

As above, the control unit 70 makes determination on each A-scan signal about the presence/absence of the IS/OS to obtain two-dimensional information on the fundus Ef in relation to the presence/absence of the IS/OS. Accordingly, an area having the photoreceptor cells with deteriorated function on the fundus is specified.

Figure 4:
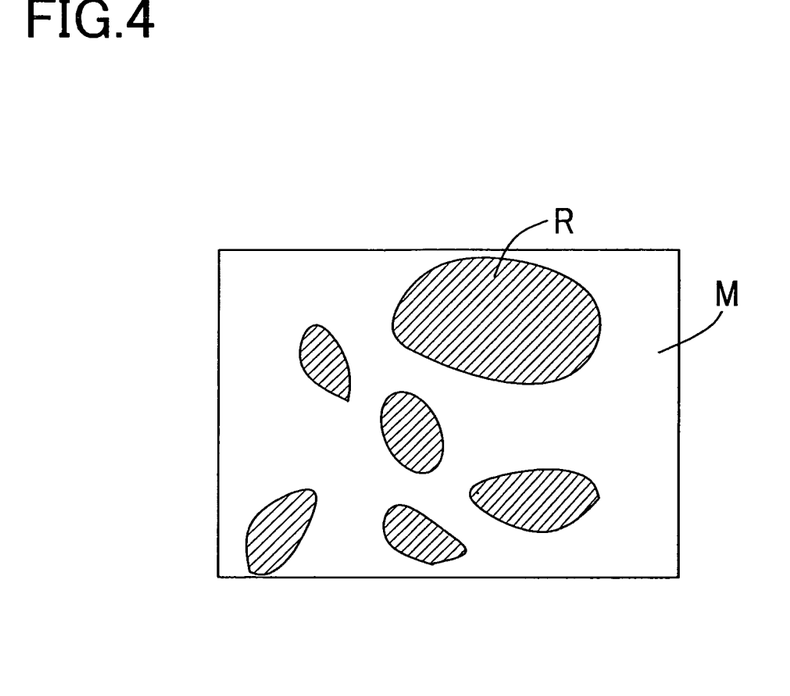
FIG. 4 is a diagram showing an analysis result of a tomographic image.

FIG. 4 is a diagram showing an analysis result of the tomographic image, i.e., an example of a map M (hereinafter, referred to as an analysis map) two-dimensionally showing a state of a visual function at each site on the fundus Ef. In this embodiment, the control unit 70 obtains, as analysis result data, the analysis map representing two-dimensional distribution data on the sites with normal/abnormal visual function. Specifically, based on the analysis result obtained as above, the analysis map representing an analysis result of a three-dimensional tomographic image is generated. The control unit 70 displays graphics (see hatching R) each denoting a site with deteriorated visual function as shown in FIG. 4. For instance, the hatching R is displayed in a specific color (e.g., red). The control unit 70 may be arranged to encircle each site with deteriorated visual function with a marker. Needless to say, the control unit 70 may display graphics each denoting a site with photoreceptor cells that normally function in the form of identifiable graphics.

The analysis result may be obtained by another configuration that an examiner himself/herself specifies a site with deteriorated visual function, as well as by the analysis using image processing. In this case, for example, while the tomographic image is displayed on the monitor 75, a site with deteriorated visual function is specified by operation of a mouse. Then, an analysis map is created based on an analysis result of the specified site. The obtained analysis map is stored in the memory 72.

<Setting Laser Irradiation Position>

The control unit 70 obtains analysis result data based on the tomographic image of the eye E imaged by the OCT device 10 before a treatment laser beam is irradiated thereto. The control unit 70 then obtains information of irradiation positions (points) of the treatment laser beam to the eye E set by use of the obtained analysis result data. Typically, the control unit 70 displays the front image obtained through the observation optical system 200 and the analysis result data in a superimposed fashion on the monitor 75.

When obtaining the analysis result data based on the tomographic image, the control unit 70 may acquire the analysis result data by analysis processing performed by the control unit 70 itself or obtain data analyzed in advance by a separate analysis device.

The touch panel of the monitor 75 is used as an operation member to allow an operator to set an irradiation area of a treatment laser beam while looking at the screen of the monitor 75. The control unit 70 obtains the information of irradiation positions of the treatment laser beam to the eye E based on an operation signal from the touch panel. It is to be noted that the operation member is not limited to the touch panel but may be any pointing device such as a mouse and a joystick.

For instance, the control unit 70 retrieves the analysis map stored in the memory 72, and then superimposes the fundus front image on this obtained analysis map and associates the analysis map and the fundus front image. Further, the control unit 70 displays a superimposed image including the analysis map and the fundus front image on the monitor 75.

The control unit 70 generates an OCT front image from the three-dimensional tomographic image used in the analysis and superimposes the created OCT front image and the analysis map, so that both data are associated with each other in pixel-to-pixel relation. The control unit 70 also may superimpose the fundus front image (e.g., an SLO image) obtained through the observation optical system 200 with the analysis map. The timing of obtaining the SLO image to be superimposed may be concurrent with the timing of obtaining the three-dimensional tomographic image or prior to actual laser irradiation performed after various tests. The obtained front image is stored as a still image in the memory 72.

Figure 5A:
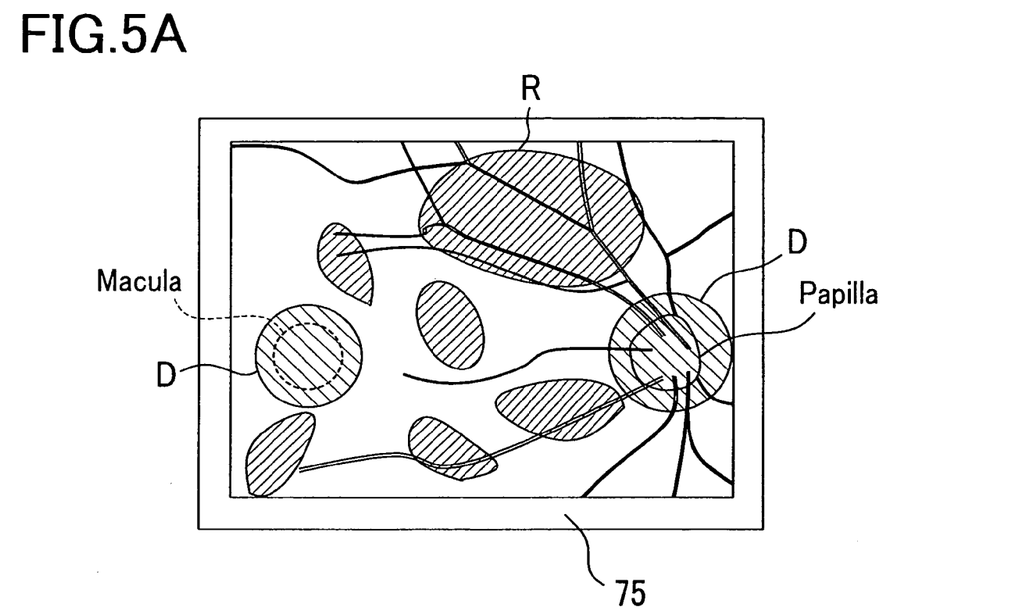
FIGS. 5A and 5B are diagrams showing a display screen in which an analysis map and an irradiation prohibited area are displayed on a fundus front image and a display screen in which a laser irradiation area is set.

For instance, the control unit 70 makes matching between the created OCT front image and the fundus front image obtained through the observation optical system 200, and adjusts a relative position between the analysis map M and the fundus front image. To be concrete, the analysis map M is superimposed on the still image representing the front image by image processing and then this superimposed image is displayed on the monitor 75. At that time, for example, based on positional information on the normal/abnormal sites of visual function, the control unit 70 displays a mark denoting a laser irradiation area in a position at which the visual function is determined to be abnormal while displays a mark denoting a laser irradiation prohibited area in a position at which visual function is determined to be normal. FIG. 5A is a diagram showing an example of the monitor 75 in which the analysis map M and irradiation prohibited areas D are displayed on the fundus front image.

The examiner sets the laser irradiation area while looking at the superimposed image displayed on the monitor 75. Specifically, the examiner first searches a treatment area while observing the fundus front image displayed on the monitor 75, and sets the laser irradiation area. At that time, the examiner sets the laser irradiation area by using the touch panel (the operation part) on the monitor 75. Upon receipt of a signal from the touch panel, the control unit 70 displays graphics G indicating the laser irradiation area on the superimposed image and also sets the specified position as the irradiation area (see FIG. 5B). A setting method using the screen may include for example a method in which a targeted region is touched so that the vicinity of the touched region is set as the irradiation area, and a method in which the outline of a targeted region is traced so that the traced region is set as the irradiation area. Alternatively, it may be arranged for the examiner to set a region not targeted for irradiation (the irradiation prohibited area) so that a region excepting the irradiation prohibited area is irradiated by laser.

Figure 5B:
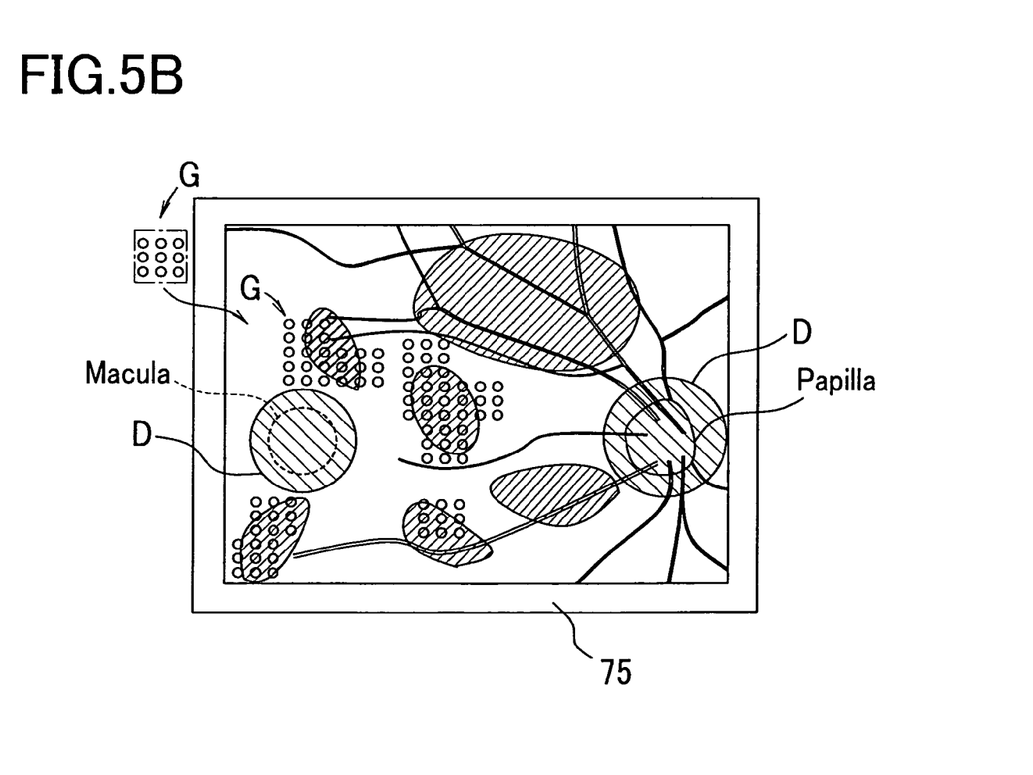

At that time, the control unit 70 sets a site with photoreceptor cells that normally function as the irradiation prohibited area D and displays a graphic denoting the irradiation prohibited area D on the analysis map (see FIG. 5B). In this case, even when the laser irradiation area G is set to include the irradiation prohibited area D, the control unit 70 excludes the irradiation prohibited area D from the laser irradiation area G. In the case where many sites have normal photoreceptor cells, the laser irradiation is restricted, which may result in insufficient treatment. Therefore, the control unit 70 may be arranged to arbitrarily unlock the irradiation prohibited area D. Further, since the examiner can grasp the state of visual function of the eye E from the analysis map and others, the examiner may also arbitrarily exclude a portion with normal photoreceptor cells from the irradiation prohibited area.

The control unit 70 may specify a predetermined site (e.g., macular, papilla) of a fundus in the three-dimensional tomographic image by image processing and set the specified site as the irradiation prohibited area D. For example, the macular and the papilla can be extracted from respective positions, luminance values, shapes, and others in the tomographic image. The macula is darker in luminance than its peripheral portion and is circular and thus, by the image processing, an image area conforming to those characteristics is extracted. The papilla is brighter than its peripheral portion and is circular and thus, by the image processing, an image area conforming to those characteristics is extracted. The control unit 70 also may specify the macular and the papilla by image processing using the fundus front image (e.g., an SLO image) and set the specified sites as the irradiation prohibited areas D.

In the present embodiment, the control unit 70 detects the positions of the macular and the papilla and sets the irradiation prohibited areas D. As an alternative, the examiner may select the positions of the macular and the papilla while observing the fundus image displayed on the monitor 75 and set them as the irradiation prohibited areas D.

At that time, the control unit 70 displays the analysis map on the fundus front image and also sets the irradiation prohibited areas based on the positions of the macular and the papilla. An image representing the irradiation prohibited area is created and displayed on the fundus front image. It is to be noted that the macular and the papilla are detected for example based on data obtained when the OCT front image and the SLO image are analyzed.

When the analysis map M and the fundus front image are associated with each other, analysis information about each pixel of the fundus front image is given. Herein, a corresponding relationship between a positional coordinate on the fundus front image and a scanning position of the optical scanner 108 has been determined in advance. Therefore, the scanning position of the optical scanner 108 and the positional coordinate on the analysis map can be associated with each other. Accordingly, the scanning position (scanning angle) of the laser beam to be scanned by the optical scanner 108 and the analysis information on the analysis map are associated with each other. For example, a portion with deteriorated visual function is associated with the irradiation point of the laser beam.

<Laser Irradiation>

The control unit 70 controls operations of the light source and the optical scanner 108 to irradiate the laser beam to the eye E based on the irradiation position information obtained as above.

For instance, when the laser irradiation area and the prohibited area are set as above, the examiner operates the operation part 76 to establish a laser irradiation mode for performing laser irradiation. Herein, the control unit 70 carries out laser irradiation based on the set irradiation area.

The control unit 70 controls the observation optical system 200 to obtain the fundus front image. The control unit 70 then displays the continually obtained fundus front image on the monitor 75 in real time. The fundus front image associated with the analysis map is used as a reference image to track the laser beam.

When the examiner operates an irradiation start key on the operation part 76, the control unit 70 is enabled to irradiate a laser beam to the set laser irradiation area G. The photocoagulation laser device 400 is configured to emit a treatment laser beam (e.g., a wavelength of 532 nm), which is delivered into the optical fiber 401 and emitted from the emission end 401a. The laser beam emitted from the emission end 401a is reflected by the dichroic mirror 30 and then irradiated to the fundus Ef via the optical scanner 108 and other optical components of the measurement optical system 106.

The control unit 70 controls the optical scanner 108 to adjust the scanning position of the optical scanner 108 onto the irradiation area G. The control unit 70 then controls the laser device 400 to irradiate a laser beam toward the irradiation area G. When a plurality of irradiation areas are present, the control unit 70 sequentially irradiates the laser beam to the irradiation areas.

At that time, the control unit 70 does not always need to irradiate the laser beam all over the irradiation area G and may also irradiate the laser beam in a pattern of dots arranged at predetermined intervals. Further, as another laser beam irradiation method, the control unit 70 may cause the optical scanner 108 to perform raster scan and irradiate the laser beam when a scanning position reaches the irradiation area G.

During laser irradiation, the control unit 70 sets the fundus image associated with the analysis map as a reference image and detects a relative position with a continually captured fundus image. The control unit 70 then controls the operations of the light source and the optical scanner 108 to irradiate the laser beam to the eye E based on the set irradiation position information. Specifically, the control unit 70 compensates the scanning position of the optical scanner 108 (tracking of the laser beam) based on a detection result so that a set area on the fundus Ef is irradiated even when the eye E moves. Thus, the laser irradiation position is compensated. For example, the control unit 70 detects displacement in surface direction (X-Y directions) of the fundus between the associated fundus front image and the continually captured fundus image, and compensates the scanning position of the optical scanner 108 to compensate the detected displacement.

The control unit 70 may be configured to change a scan speed for laser irradiation during image obtaining by the optical scanner 108 and a scan speed for image capture by the OCT optical system 100. For example, the scan speed for laser irradiation is set slower than the scan speed for image capture by the OCT optical system 100.

The above configuration enables treatment laser irradiation utilizing the layer analysis result of the tomographic image obtained by the OCT. Accordingly, laser treatment can be performed based on the information that could not be visually recognized by the observation of the fundus front image. Thus, a good operative result can be achieved.

For example, as mentioned above, since the analysis result related to the condition of photoreceptor cells is utilized, it is possible to reduce death of the photoreceptor cells caused by laser irradiation. This helps the recovery of visual performance after the operation.

If a site with photoreceptor cells that do not work properly is specified in advance as described above, a trial shot of a laser beam for checking the state of coagulation can be directed to the site with photoreceptor cells that do not work properly. Thus, the trial shot can be effectively conducted.

In the above explanation, the analysis of the visual function is performed by detecting the IS/OS; however, the present invention is not limited thereto. For example, the control unit 70 may be configured to detect a ganglyocyte layer and an optic nerve fiber layer by image processing and determine whether the thicknesses of those layers are normal or not. The control unit 70 then obtains an analysis map related to visual function based on a determination result at each position.

As another alternative, the control unit 70 may be configured to measure information on changes in tomographic image before and after the fundus is stimulated and make analysis on visual function. In this case, the apparatus is provided with a stimulation light source (e.g., a visible light source) that emits light for stimulating the fundus.

For instance, the control unit 70 controls the stimulation light source to capture a tomographic image before stimulation and a tomographic image after stimulation. Then, a change in luminance between the tomographic images obtained before and after stimulation is calculated. Based on an amount of change in luminance, the control unit 70 then determines whether the visual function is normal or not. The control unit 70 may also be configured to continually capture tomographic images from before stimulation up to after a predetermined time elapsed from the termination of stimulation, and conduct determination related to visual function based on the captured tomographic images.

In the above explanation, the control unit 70 may also configured to superimpose the fundus front images continually obtained as a moving image through the observation optical system 200 and the analysis map. Such moving image is effective for an operator in choosing a laser irradiation area while looking at the moving image and irradiating a laser beam to the fundus.

Herein, the control unit 70 sets the fundus image associated with the analysis map, as a reference image, and detects a relative position with the fundus continually captured image. Based on a detection result thereof, the control unit 70 compensates a displaying position of the analysis map so that a corresponding relationship between the sites of the fundus and the analysis map coincides between before and after the eye moves.

For instance, the control unit 70 moves the analysis map based on a detected positional displacement amount of the eye by image processing, and then compensates the displaying position of the analysis map by an amount corresponding to the detected positional displacement amount. Therefore, even when the eye moves while the front image is being observed, a fixed analysis map can be observed on the fundus front image.

When the graphic denoting the irradiation prohibited area and/or the laser irradiation area are/is to be superimposed on the front image (a moving image), the control unit 70 may compensate a displaying position of the graphic based on the aforementioned result of detection of the relative position so that the corresponding relationship between the fundus sites and the graphic coincides even when the eye moves. Of course, when both the analysis map and the graphic are to be superimposed on the front image, their displaying positions may also be compensated.

In the above tracking, a method of detecting positional displacement between two images may be selected from various image processing methods (a method using various correlation functions, a method using Fourier transform, and a method based on matching of characteristic points).

One example of the method is conducted by displacing the position of a reference image or an observation image (a current fundus image) by one pixel each, comparing the reference image and a subject image to detect a positional displacement direction and a positional displacement amount between both data when they coincide most closely with each other (when they are in highest correlation). Another example of the method is conducted by extracting a characteristic point common between a predetermined reference image and a subject image and, based on the extracted characteristic point, detecting a positional displacement direction and a positional displacement amount.

An evaluation function in template matching may be based on SSD (Sum of Squared Difference) representing the similarities, SAD (Sum of Absolute Difference) representing the differences, or the like.

In the above explanation, the OCT optical system and the laser irradiation optical system are arranged to share part of optical systems (e.g., the optical scanner), but they are not limited to such configuration. As an alternative is to provide a first optical scanner for the OCT optical system to scan measurement light and a second optical scanner, different from the first optical scanner, for the laser irradiation optical system to scan the treatment laser beam.

Further, the OCT device and the photocoagulation laser device may be placed respectively in separate cabinets or housings. For example, a laser irradiation area is set in advance by use of the tomographic image obtained by the OCT device and then the set laser irradiation information is input to the photocoagulation laser device. It is to be noted that the laser irradiation information is input to the photocoagulation device through for example a communication line such as LAN. With this configuration, an analysis result obtained in the OCT device alone can be utilized. Needless to say, the photocoagulation laser device may be arranged to receive a tomographic image and analyze the received tomographic image, and set a laser irradiation position. Alternatively, the photocoagulation laser device may be configured to receive an analysis result and superimpose the received analysis result on a fundus front image, and set an irradiation position.

In some cases, the fundus front image obtained through the fundus observation system provided in the photocoagulation device and the analysis map (or the fundus front image associated with the analysis map) are different in imaging magnification (power), an aspect ratio, and others. In those cases, preferably, the control unit 70 compensates the imaging magnification and the aspect ratio of the analysis map (or the fundus front image associated with the analysis map) by image processing according to the fundus front image obtained through the fundus observation system.

The observation optical system 200 placed in the photocoagulation laser device may also be provided with a slit lamp through which an operator can directly observe a patient's eye. Furthermore, an in-field display may be provided for an operator who looks through eyepieces. In this case, a beam combiner is provided between the eyepieces of the slit lamp and the patient's eye. An image displayed in the in-field display is reflected by the beam combiner to travel toward the eyepieces. Thus, the operator can view an observation image through the slit lamp and the displayed image.

In such a case, the control unit 70 may be configured to display the analysis result obtained as above in the in-field display so that the fundus observation image and the analysis result are displayed in superimposed fashion. The operator therefore can determine the laser irradiation area with reference to the analysis result of the OCT while looking at the fundus image through the slit lamp.

The above explanation exemplifies the configuration that the tomographic image of the fundus is captured by the OCT device, and the laser beam is irradiated to the fundus based on the analysis result with respect to the obtained tomographic image, but the present invention is not limited thereto. Any configuration may be adopted as long as a tomographic image of an eye is captured by the OCT device and a laser beam is irradiated onto tissues of the eye based on an analysis result with respect to the captured tomographic image. An example of the configuration is arranged to capture a tomographic image of an anterior segment by the OCT device and then irradiate a laser beam to the anterior segment based on an analysis result with respect to the captured tomographic image.

In the above explanation, the analysis result is obtained by a combination of the OCT devices but may also be provided as an analysis result obtained by another type of device. For example, a result of a perimeter may be used.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

The invention claimed is:
1. An ophthalmic laser treatment apparatus comprising:
an irradiation optical system including a treatment light source and a deflector for deflecting a laser beam for treatment emitted from the light source with respect to a patient's eye, the irradiation optical system being arranged to irradiate the laser beam to an area of the eye to be treated;

a controller controls to:
(i) obtain two-dimensional analysis result data of a fundus of the patient's eye based on a three-dimensional tomographic image captured by an optical coherence tomography device before the laser beam is irradiated,
(ii) obtain an analysis map using the two-dimensional analysis result data, the analysis map being in color includes at least one of an analysis result indicating a presence or absence of a retinal layer based on the three-dimensional tomographic image and an analysis result indicating a thickness of the retinal layer based on the three-dimensional tomographic image,
(iii) set information of an irradiation position of the laser beam on a surface of the fundus based on the obtained analysis map in color;

an observation optical system for observing and obtaining a front image of the patient's eye;

a display, wherein the controller further controls to present, via the display, a superimposed image of the front image of the patient's eye positioned over the analysis map in color or a superimposed image of the analysis map in color positioned over the front image of the patient's eye; and wherein the controller further controls operation of the light source and the deflector to irradiate the laser beam to the patient's eye based on the set information of the irradiation position of the laser beam.

2. The ophthalmic laser treatment apparatus according to claim 1,
wherein the display comprises a monitor.

3. The ophthalmic laser treatment apparatus according to claim 1, further comprising an optical coherence optical system including:
a measurement light source,
a light splitter for splitting the light emitted from the measurement light source into measurement light and reference light, the measurement light being to be delivered to and reflected from the patient's eye, and
a detector for detecting an interference state between the measurement light reflected from the eye and the reference light, and
the optical coherence optical system being arranged to image a tomographic image of the eye before the treatment laser beam is irradiated.

4. The ophthalmic laser treatment apparatus according to claim 1, wherein
the apparatus is adapted to irradiate the treatment laser beam to the fundus of the patient's eye,
the optical coherence tomography device is a device for imaging a tomographic image of the fundus of the eye, and
the controller analyzes a three-dimensional tomographic image of the fundus and performs a determination processing on a normal/abnormal site of visual function to obtain position of a two-dimensional position related to the normal/abnormal site of visual function on the fundus as the analysis result data.

5. The ophthalmic laser treatment apparatus according to claim 4, wherein the display comprises a monitor,
wherein, based on the position information, the controller controls to display, on the monitor, a site of the fundus determined to be abnormal as a laser irradiation area and display a site of the fundus determined to be normal as a laser irradiation prohibited area.

6. The ophthalmic laser treatment apparatus according to claim 4, wherein the controller controls to extract a photoreceptor inner/outer segment layer by processing of the three-dimensional tomographic image, and determine whether the photoreceptor inner/outer segment layer is present or not to obtain the position information as the analysis result data.

7. The ophthalmic laser treatment apparatus according to claim 1,
wherein the controller controls to set a fundus image associated with the analysis map in color which also represents the position information, as a reference image, detect a relative position between the front image obtained through the observation optical system and the reference image, and compensate a scanning position by the deflector based on the detected relative position on the monitor.

8. The ophthalmic laser treatment apparatus according to claim 7, wherein an image magnification and an aspect ratio of the analysis map are compensated based on the front image.

9. The ophthalmic laser treatment apparatus according to claim 1, wherein
the controller controls to set a fundus image associated with the analysis map, as a reference image, detect a relative position between the front image obtained through the observation optical system and the reference image, and compensate a displaying position of the analysis map based on the detected relative position.

10. The ophthalmic laser treatment apparatus according to claim 1, further including an image generator for generating an OCT front image from the three-dimensional tomographic image,
wherein the controller controls to perform matching between the OCT front image generated by the image generator and the front image obtained through the observation optical system to adjust a relative position between the analysis map and the front image.

11. The ophthalmic laser treatment apparatus according to claim 1, wherein the controller includes an operation part that allows an operator to set an irradiation area of the treatment laser beam while viewing a screen of the monitor, and the controller controls to set position information based on an operation signal from the operation part.

12. The ophthalmic laser treatment apparatus according to claim 1,
wherein the front image of the patient's eye obtained through the observation optical system includes a still image of the front image of the patient's eye; and
wherein the display comprises a monitor,
wherein the controller controls to display, on the monitor, the superimposed image of the still image of the front image over the analysis map in color or the superimposed image of the analysis map in color positioned over the still image of the front image.

13. The ophthalmic laser treatment apparatus according to claim 1,
wherein the display comprises a touch panel monitor,
wherein the controller controls to display, on the touch panel monitor, the superimposed image of the obtained still image of the front image and the analysis map in color and set irradiation position information.

14. The ophthalmic laser treatment apparatus according to claim 1, wherein the controller controls operation of the light source and the deflector to irradiate the laser beam in a pattern of dots.

15. The ophthalmic laser treatment apparatus according to claim 1,
wherein the front image of the patient's eye obtained through the observation optical system includes a moving image of the front image of the patient's eye; and
wherein the display comprises a monitor,
wherein the controller controls to display, on the monitor, the superimposed image of the moving image of the front image and the analysis map in color.

16. The ophthalmic laser treatment apparatus according to claim 15,
the controller controls to (i) set a fundus image associated with the analysis map in color which also represents the position information, as a reference image, (ii) continually detect a relative position between the front image obtained through the observation optical system and the reference image, and (iii) compensate a scanning position by the deflector based on the detected relative position on the monitor.

17. The ophthalmic laser treatment apparatus according to claim 1, wherein the optical coherence tomography device and the ophthalmic laser treatment apparatus are placed respectively in separate cabinets or housings, and
wherein the ophthalmic laser treatment apparatus is configured to receive at least the analysis map in color and superimpose the analysis map in color onto the front image, such that the analysis map in color lays over the front image.

18. The ophthalmic laser treatment apparatus according to claim 1, wherein the observation optical system comprises an ophthalmic scanning laser optometry or a fundus camera.

19. The ophthalmic laser treatment apparatus according to claim 1, wherein the analysis map represents an analysis result of the three-dimensional tomographic image.

* * * * *